(12) United States Patent
Krattiger et al.

(10) Patent No.: US 7,435,218 B2
(45) Date of Patent: Oct. 14, 2008

(54) OPTICAL INSTRUMENT, IN PARTICULAR AN ENDOSCOPE, HAVING AN INTERCHANGEABLE HEAD

(75) Inventors: Beat Krattiger, Beringen (CH); Manfred Kuster, Schaffhausen (CH); Harald Haan, Schaffhausen (CH)

(73) Assignee: Storz Endoskop GmbH (CH)

( * ) Notice: Subject to any disclaimer, the term of this patent is extended or adjusted under 35 U.S.C. 154(b) by 0 days.

(21) Appl. No.: 10/694,577

(22) Filed: Oct. 27, 2003

(65) Prior Publication Data
US 2004/0143162 A1 Jul. 22, 2004

Related U.S. Application Data

(63) Continuation of application No. PCT/EP02/04664, filed on Apr. 26, 2002.

(30) Foreign Application Priority Data

Apr. 27, 2001 (DE) ................. 101 21 450

(51) Int. Cl.
*A61B 1/00* (2006.01)
*A61B 1/06* (2006.01)
(52) U.S. Cl. ............. 600/175; 600/129; 600/179; 600/182
(58) Field of Classification Search ........ 600/136, 600/129, 175, 182, 179; 348/72, 74, 75
See application file for complete search history.

(56) References Cited

U.S. PATENT DOCUMENTS 4,425,375 A * 1/1984 Abramson ............... 427/494
4,706,653 A 11/1987 Yamamoto ................. 128/4
4,856,495 A * 8/1989 Tohjoh et al. ............ 600/175
4,919,114 A * 4/1990 Miyazaki ................ 600/110
4,941,457 A * 7/1990 Hasegawa ............... 600/142
4,947,245 A * 8/1990 Ogawa et al. ............ 348/66
5,188,093 A * 2/1993 Lafferty et al. .......... 600/109
5,379,756 A * 1/1995 Pileski et al. ........... 600/109
5,512,036 A * 4/1996 Tamburrino et al. ...... 600/172
5,547,457 A * 8/1996 Tsuyuki et al. .......... 600/175
5,916,148 A * 6/1999 Tsuyuki ................. 600/176
5,961,445 A * 10/1999 Chikama ................ 600/112
6,095,970 A 8/2000 Hidaka et al. ........... 600/110
6,142,930 A 11/2000 Ito et al. ................. 600/109
6,184,923 B1 2/2001 Miyazaki ................. 348/75
6,206,825 B1 * 3/2001 Tsuyuki ................. 600/182
6,361,491 B1 * 3/2002 Hasegawa et al. ........ 600/175
6,554,767 B2 * 4/2003 Tanaka ................. 600/175

FOREIGN PATENT DOCUMENTS

DE           29 613 103      10/1997

* cited by examiner

*Primary Examiner*—John P Leubecker
(74) *Attorney, Agent, or Firm*—St. Onge Steward Johnston & Reens LLC

(57) ABSTRACT

An optical instrument, in particular an endoscope, has a shaft and an inter-changeable head. The interchangeable head is detachably connected to the distal end of the shaft at a coupling point. The instrument also has a first transmission system for distal transmission of illuminating power, and a second transmission system for proximal transmission of image information, the first transmission system and the second transmission system passing through the coupling point. The interchangeable head and/or the coupling point are/is designed in such a way that upon loosening of the interchangeable head image information of perceptively modified quality is transmitted by the second transmission system.

9 Claims, 7 Drawing Sheets

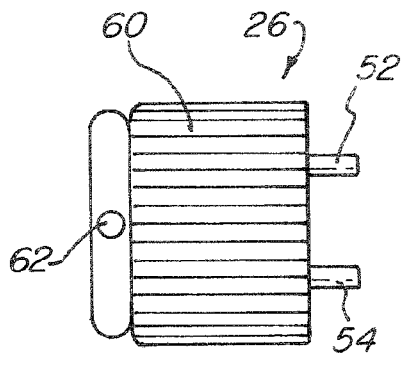
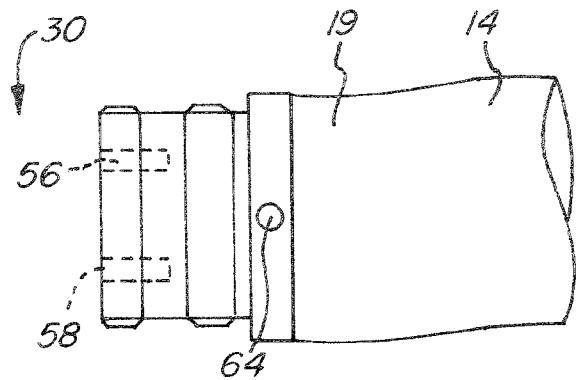
FIG. 2a    FIG. 2b
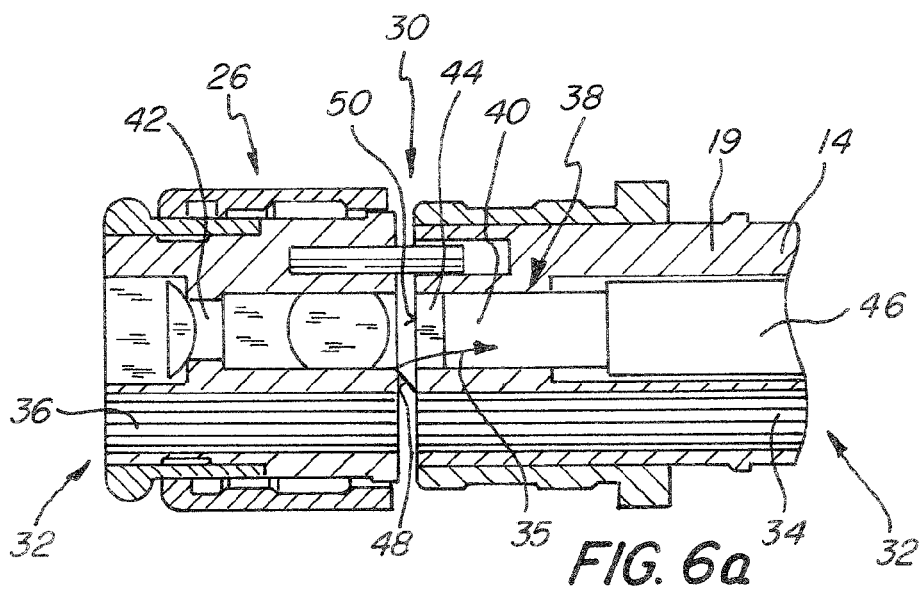
FIG. 6a
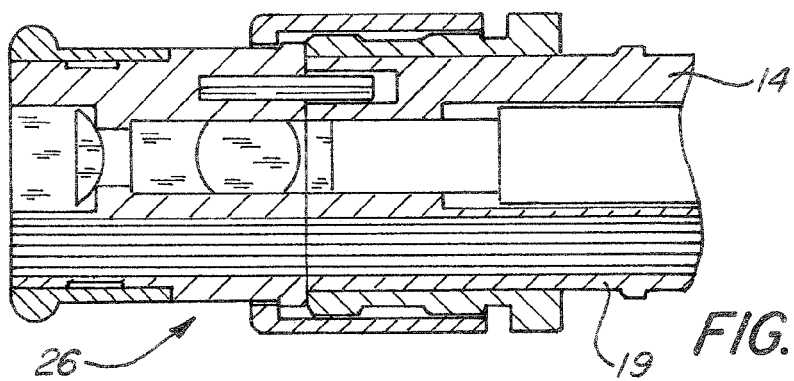
FIG. 6b

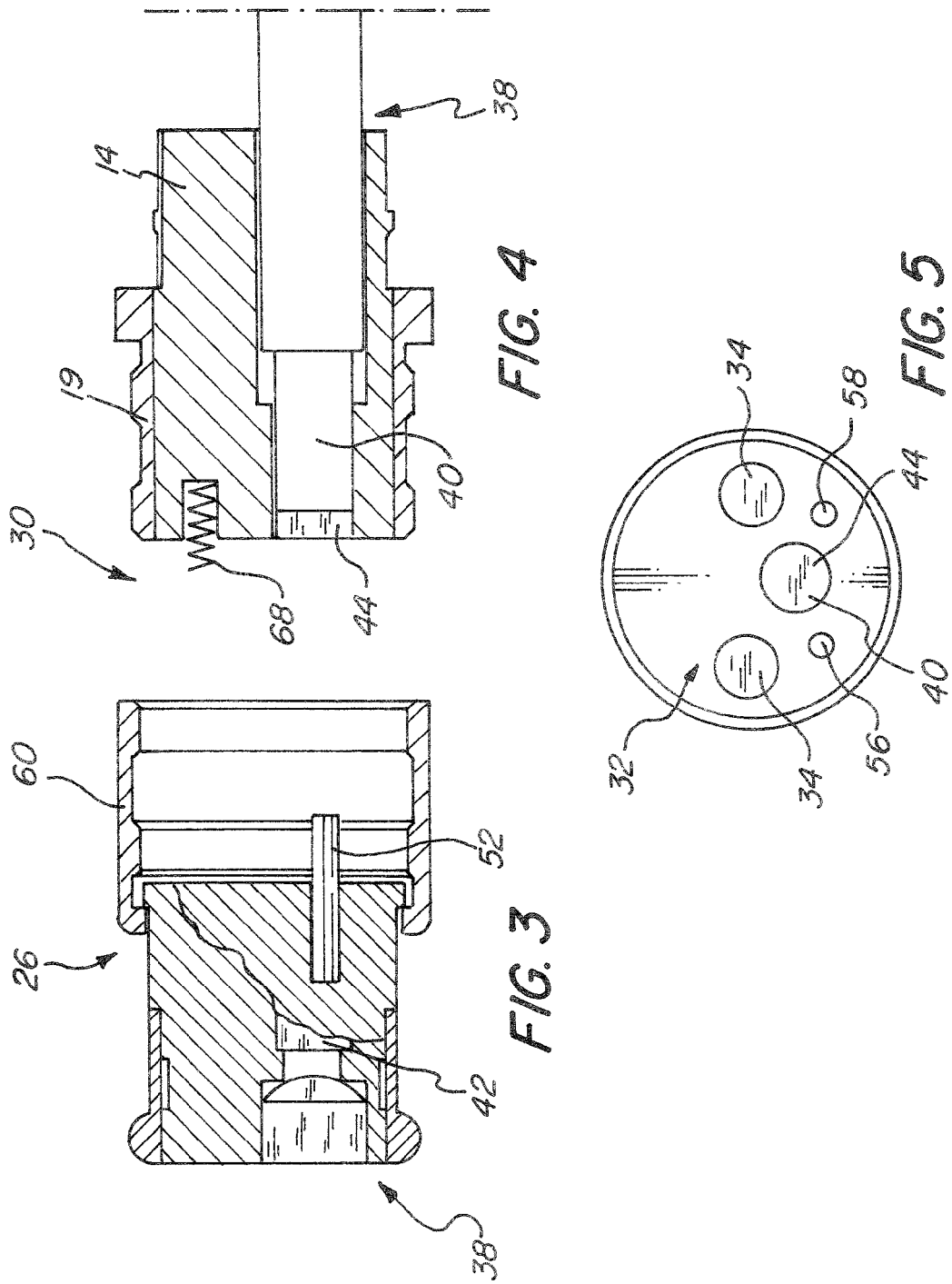

OPTICAL INSTRUMENT, IN PARTICULAR AN ENDOSCOPE, HAVING AN INTERCHANGEABLE HEAD

The present application is a continuation of pending international patent application PCT/EP02/04664 filed on Apr. 26, 2002 which designates the United States, and which claims priority of German patent application 101 21 450.2 filed on Apr. 27, 2001.

BACKGROUND OF THE INVENTION

The invention relates to an optical instrument and in particular to an endoscope.

The invention more specifically relates to an optical instrument, having a shaft and having an interchangeable head that is detachably connected to the distal end of the shaft at the coupling point, and having, furthermore, a first transmission system for transmission of illuminating power in distal direction and having a second transmission system for transmission of image information in proximal direction, the first transmission system and the second transmission system passing through the coupling point.

Such an optical instrument, in particular an endoscope, is generally known through its use, the interchangeable heads being interchangeable objectives or supplementary lenses in the case of known instruments without the invention being limited thereto.

Although the present invention is described using the example of an endoscope, the invention is not limited to an endoscope, but rather can be used generally in optical instruments or devices.

Endoscopes are used for medical purposes, on the one hand, and for technical purposes, on the other hand. In medicine, endoscopes are used in minimally invasive surgery for visual control of operations. In the technical field, endoscopes are used to investigate cavities that are difficult to access, in particular to investigate operating cycles in engines, turbines and in reaction chambers, including during their operation.

Furthermore, known endoscopes include those with a rigid shaft and those with a flexible shaft, it being possible for endoscopes with a flexible shaft to be introduced to the place of use through winding paths, and also various viewing directions being made possible by means of a deflecting mechanism.

Endoscopes are usually fitted with a first transmission system for transmission of illuminating power in distal direction, and with a second transmission system for transmission of image information in proximal direction. It is normally incoherent fiber bundles, that is to say optical waveguides that are used as the first transmission system for transmitting illuminating power. However, within the meaning of the present invention, illuminating power is also understood as electric power used to feed a light source on or in the endoscope. In the case of endoscopes, the transmission system for transmitting image information comprises either lenses, coherent bundles of optical fibers, that is to say so-called image waveguides, electric lines that conduct in the proximal direction electric signals generated by a distally arranged image pick-up, lightwave data lines, or teletransmissions by means of temporally modulated radio waves or temporally modulated light.

With known endoscopes, there is usually also present at the distal end of the shaft of the endoscope an imaging optics that images the space to be observed onto the start of the transmission link, for example onto a fiber bundle.

The imaging optics used, which is not exchangeable, fixes the direction of view and the field of view. In order to configure an existing endoscope in a more versatile fashion with regard to direction of view, field of view and working distance, endoscopes are currently being offered with interchangeable heads in the form of interchangeable objectives, it being possible to vary the direction of view, the field of view and the working distance by selecting an appropriate interchangeable objective. The possibilities of use of the endoscope, which is not infrequently very expensive, can be widened in this way by keeping various interchangeable objectives at the ready.

The interchangeable objectives of the known endoscopes, in particular in accordance with U.S. Pat. No. 4,706,653, are not independent optics, but are designed only as supplementary lenses of telephoto or wide-angled nature such as are known from photography. The interchangeable objectives of the known endoscopes also include, for example, deflecting optics in order to be able to switch over from a straight ahead direction of view without interchangeable objective to a lateral direction of view with an interchangeable objective coupled on. In the case of interchangeable objectives of the known endoscopes, there are also included, if appropriate, in addition to the imaging optics optical waveguides and optical elements for illumination that adapt the illuminating light to the field of view.

In order to avoid the leakage of illuminating light into the observing optics at the coupling point, in the case of the known endoscopes a staircase-like spatial graduation at the coupling point has mostly been provided between the light transmission system and image transmission system.

A substantial problem with endoscopes that are fitted with interchangeable objectives is the risk of an overlooked loss of the interchangeable objective when the latter becomes undesirably loosened from the distal end of the shaft of the endoscope. In the case both of endoscopes for medical purposes and of endoscopes for technical purposes, an overlooked loss of the interchangeable objective in the area of observation, that is to say in the case of medical endoscopes in human or animal bodies, and in the case of technical endoscopes, for example, when the endoscope is used in aircraft maintenance during engine inspection, is associated with devastating consequences in some circumstances.

Various antiloss safeguards such as bayonet closures, subdivided threads, subdivided left/right threads and thread/bayonet combinations have been developed to solve this problem in the case of known endoscopes.

Apart from the fact that such antiloss safeguards render it difficult to mount the interchangeable objectives on the shaft of the endoscope because of the small dimensions of the interchangeable objectives in the case of endoscopes, such antiloss safeguards do not completely solve the problem of the overlooked loss, since in the event of failure of the antiloss safeguards it is possible nevertheless for the interchangeable objective to come loose from the shaft of the endoscope without this being noticed.

As already mentioned previously, optical instruments, in particular endoscopes, are also known in the case of which the transmission system has for the purpose of proximal transmission of image information at least one electronic image pick-up that is arranged in the region of the distal end of the shaft such as is known, for example, from U.S. Pat. No. 5,379,756. In this known endoscope, an imaging optics is connected upstream of the image pick-up, which is not exchangeable, at the distal end of the shaft. This endoscope has no interchangeable head. Document U.S. Pat. No. 6,184,923 discloses a comparable optical instrument in the form of an endoscope having an electronic image pick-up, this endoscope containing at the distal end an interchangeable head that has an imaging optics for imaging the area of observation onto the image pick-up. Thus, in this instrument only the imaging optics is exchangeable, but not the image pick-up. However, the production costs of the shaft with permanently integrated image pick-up or a camera are increased thereby.

SUMMARY OF THE INVENTION

In accordance with one aspect, the invention is based on the object of developing an optical instrument, in particular an endoscope, to the effect that the risk of an overlooked loss of the interchangeable head is avoided.

Irrespective of the aim of indicating to the user of the optical instrument a loosening of the interchangeable head by a loss of image quality, according to a further aspect it is an object of the present invention to develop an optical instrument, in particular an endoscope, to the effect that the instrument can be produced with lower costs, at least with regard to the shaft.

According to a first aspect of the present invention, an optical instrument is provided, comprising a shaft having a distal end, an interchangeable head detachably connected to said distal end of said shaft at a coupling point, a first transmission system for transmission of illuminating power in distal direction, said first transmission system being arranged partially in said shaft and partially in said interchangeable head and passing through said coupling point, a second transmission system for transmission of image information in proximal direction, said second transmission system being arranged partially in said shaft and partially in said interchangeable head and passing through said coupling point, at least one of said interchangeable head and said coupling point being designed in such a way that upon loosening of said interchangeable head image information of perceptively modified quality is transmitted by said second transmission system.

According to another aspect of the present invention, an optical instrument is provided, comprising a shaft having a distal end, an interchangeable head detachably connected to said distal end of said shaft at a coupling point, a first transmission system for transmission of illuminating power in distal direction, said first transmission system being arranged partially in said shaft and partially in said interchangeable head and passing through said coupling point, a second transmission system for transmission of image information in proximal direction, said second transmission system being arranged partially in said shaft and partially in said interchangeable head and passing through said coupling point, wherein said second transmission system has an imaging optics, said imaging optics being arranged partially in said interchangeable head and partially in said shaft, at least one of said interchangeable head and said coupling point being designed in such a way that upon loosening of said interchangeable head image information of perceptively modified quality is transmitted by said second transmission system.

According to another aspect of the invention, an optical instrument is provided, comprising a shaft having a distal end, an interchangeable head detachably connected to said distal end of said shaft at a coupling point, a first transmission system for transmission of illuminating power in distal direction, said first transmission system being arranged partially in said shaft and partially in said interchangeable head and passing through said coupling point, a second transmission system for transmission of image information in proximal direction, said second transmission system being arranged partially in said shaft and partially in said interchangeable head and passing through said coupling point, wherein said second transmission system has at least one image pick-up that is arranged in said interchangeable head, and an electric signal line that leads from said image pick-up through said coupling point in proximal direction.

The solution according to the invention is based on the principle of indicating to the user a loosening of the interchangeable head that can lead to complete detachment from the shaft of the endoscope simply by virtue of the fact that the observed image is modified in a qualitatively perceptible fashion upon loosening of the interchangeable head. Such a modification of the observed image can be expressed by virtue of the fact that the image becomes brighter and of weaker contrast, darker, worse and/or more blurred, or even disappears. The way in which the transmitted image information changes upon loosening of the interchangeable head depends on the principle on which the transmission of the illuminating power and/or the transmission of the image information are/is based, as emerges from the following description of preferred refinements of the invention. The solutions according to the invention therefore depart from the concept of providing only an antiloss safeguard at the coupling point between the interchangeable head and the shaft of the endoscope. In the case of the known endoscopes, a loosening of the interchangeable head from the shaft of the endoscope can, by contrast, not be noticed on the basis of the transmitted image information, since the interchangeable heads of the known endoscopes are designed merely as supplementary lenses. This is because in the known endoscopes the image sharpness and the contrast are maintained given an interchangeable objective that is coming loose or has fallen off, and the field of view is changed only slightly, something which is scarcely perceptible if attention is not exclusively focused thereon. In the event of unexpected loosening, the change in the field of view remains overlooked, since the operation is not influenced.

In a preferred refinement, the second transmission system has an imaging optics, the imaging optics being arranged partially in the interchangeable head and partially in the shaft, the part of the imaging optics arranged in the shaft being exchangeable.

In the case of this refinement, as well, in which the second transmission system constitutes an optical system, a loosening of the interchangeable head is indicated to the user by a worsening of the image, that is to say by a blurry image. The image can then disappear again entirely in the event of a loss of the interchangeable head. The advantage of the partial distribution of the imaging optics over the interchangeable head and over the shaft has the advantage that the interchangeable head can be implemented in a simplified way and at lower cost, and this leads overall to a reduction in the cost of the optical instrument, since a part of the imaging optics need be provided only once, specifically in the shaft of the instrument.

The exchangeability of the part of the imaging optics arranged in the shaft has the advantage that the endoscope can be readapted if necessary to a new future range of interchangeable heads.

As is provided in a further preferred refinement, the invention can advantageously be used even when the second transmission system has an image pick-up that is arranged in the interchangeable head, and an electric signal line from the video image sensor in the proximal direction, the coupling point then being designed such that upon loosening of the interchangeable head the signal line is interrupted in the proximal direction.

In the case of such a refinement, the image information is transmitted starting from the electronic image pick-up by electric signals into which the optical signals received by the image pick-up have previously been converted. The coupling point can be designed, for example, with one or more contacts in such a way that upon loosening of the interchangeable head at least one contact is opened and thereby the transmitted image information is modified, for example a segment of the image or the entire image disappears.

Whereas in the case of the endoscopes known in the prior art the image pick-up, for example in the form of a CCD chip, is integrated in the shaft, and the imaging optics connected upstream of the image pick-up can be exchanged, if necessary, the inventive refinement mentioned above has the advantage that, because of the integration of the at least one image pick-up in the interchangeable head, it is also possible to design the interchangeable head as a part subject to wear when the optical instrument is used under harsh conditions. Moreover, the shaft of the instrument can be produced in a particularly cost-effective fashion, since it need not contain optical components of any sort, not even the image pick-up itself.

Preference is given here to the signal line being designed as a plug-in contact in the region of the coupling point.

In this way, the image pick-up can then be connected to the shaft of the instrument in a way that is easy to handle in a signal-conducting fashion.

In a further preferred refinement, the at least one image pick-up is a miniaturized camera.

The development of complete, autonomous camera units is heading toward miniaturized designs that are particularly suitable for use in an interchangeable head of an endoscope, since endoscopes always have to be of the slimmest possible design. Using such miniaturized camera modules is therefore advantageous particularly in the case of endoscopes.

In a preferred refinement, the first transmission system comprises an optical waveguide that extends through the shaft and through the interchangeable head, and is interrupted at the coupling point, and the distal end of the shaft and the interchangeable head each have a flat, preferably polished surface at the coupling point.

In the case of this preferred refinement, the loosening of the interchangeable head becomes noticeable by a brightening and attendant turbidity (contrast weakening) of the transmitted image information when the basis of the second transmission system for transmitting the image information is an image waveguide system based on fibers or lenses. Whereas in the case of existing interchangeable heads in the form of interchangeable objectives the light transmission and image transmission systems situated close to one another are delimited in staircase fashion for the purpose of mutual separation, it has been found that through diffraction and absorption flat polished boundary surfaces permit a certain small slit width (other than zero) below a critical slit width without the occurrence of image degradation. The manufacturing tolerances permit the slit width to be kept below this critical slit width in conjunction with a tightened connection between the interchangeable head and the distal end of the shaft. This effect of image impairment does not occur until loosening of the interchangeable head occurs, that is to say given an increasing slit spacing when the critical slit width is exceeded. If the interchangeable head is then loosened, illuminating light is reflected into the image transmission system owing to this measure because of the enlargement of the slit between the interchangeable head and shaft, as a result of which the user experiences a loosening of the interchangeable head through the image turbidity and is warned. A further advantage of this measure consists in that the interior is additionally sealed against the ingress of liquids and dusts owing to the matching seating of the interchangeable head and the shaft. Moreover, the flat locating surface between the interchangeable head and shaft can be produced more easily than the staircase-like stepped seating, provided with conventional endoscopes, between the interchangeable head and the shaft.

In a further preferred refinement, the second transmission system has an imaging optics, the imaging optics being arranged entirely in the interchangeable head.

This measure has the advantage that even a slight loosening of the interchangeable head, for example a slight distancing or tilting, has the effect that the image can clearly be detected as degraded by defocusing. In the event of a complete loss of the interchangeable head, it is even the case that no further image is transmitted. What is important, however, is that in the event of a loosening of the interchangeable head the degradation of the image already warns the user about the possibility of losing the interchangeable head, and so he can withdraw the endoscope in good time from the observation space before the interchangeable head is lost. In this inventive refinement, there are thus no optically imaging elements in the shaft of the endoscope, and so the endoscope cannot be used without an interchangeable head.

The previously mentioned refinements, in which the second transmission system has an imaging optics, can also preferably be used in those optical instruments in which the second transmission system has an electronic image pick-up that is arranged in the shaft of the instrument. Upon loosening of the interchangeable head, the imaging of an object onto the image pick-up is disturbed such that a degraded image is noticed in this case, as well, as soon as the interchangeable head is loosened. Also, in the case of such a refinement the imaging optics can be arranged, in turn, partially in the interchangeable head and partially in the shaft upstream of the image pick-up.

In a further preferred refinement, the first transmission system has a light source and an electric power line from the proximal end to the light source, the light source being arranged in the interchangeable head, and the coupling point is designed such that upon loosening of the interchangeable head the signal line is interrupted in the distal direction.

In a way resembling the previously mentioned refinement, in this refinement the first transmission system is likewise based on a transmission of electric power, the light source then being arranged in the interchangeable head, for example in the form of an LED. Upon loosening of the interchangeable head, the electric power line can be interrupted, for example by providing appropriate contacts between the interchangeable head and the distal end of the shaft in the region of the coupling point.

In a further preferred refinement, the interchangeable head is connected to the distal end of the shaft at the coupling point by means of at least one positioning pin that engages in a corresponding bore.

It is advantageous in this case that the interchangeable heads can be positioned exactly when being coupled to the shaft so that image sharpness and image alignment are correct. An out-of-round positioning pin with a correspondingly complementary bore can suffice to fulfill this purpose. However, at least two positioning pins are preferred, the result being that the interchangeable head can be centered even more accurately and, moreover, secured exactly in terms of rotation. Moreover, the positioning pins open up the additional possibility of being used for transmission of electric signals and power. In the known endoscopes, securing the interchangeable objective in terms of rotation is achieved by means of an index groove on the circumference of the shaft or of the interchangeable objective, the centering being achieved by accurate fitting of the diameters. The positioning of the interchangeable objective in the case of the known endoscopes thus requires two independent elements that each need to be recessed with the required precision. However, this is expensive in terms of production, since complicated machines and operating cycles are required.

In a further preferred refinement, the at least one positioning pin is exchangeable.

It is advantageous in this case that in the event of damage to or bending of the positioning pin it is necessary to exchange only the latter without the interchangeable head as a whole becoming unusable. By contrast, in the case of the known endoscopes, in which the interchangeable objectives are secured in terms of rotation by means of cams and index grooves, there is the risk of the cams breaking off during alignment, and of the interchangeable objective as a whole becoming unusable.

In a further preferred refinement, the at least one positioning pin serves the purpose of transmitting electric signals or electric power.

This measure is advantageous, in particular, in the case of a refinement of the image transmission system of the inventive endoscope with an optoelectronic image pick-up (video image sensor) in the interchangeable head, since the at least one positioning pin can be used to perform transmission of electric signal s and power that can, moreover, easily be severed and restored.

Consequently, when the interchangeable head has an optoelectronic image pick-up (video image sensor or complete camera), it is preferred in accordance with a further refinement for the transmission of electric signals through the coupling point to be performed by the at least one positioning pin.

The connection of the interchangeable head to the shaft of the endoscope via the at least one positioning pin and the bore can advantageously be designed in such a way that upon loosening of the interchangeable head transmission of electric signals through the coupling point is interrupted.

In the case of one refinement of the interchangeable head having an optoelectronic image pick-up, this measure constitutes an advantageously simple measure for interrupting the image transmission upon loosening of the interchangeable head so that upon loosening of the interchangeable head the user is immediately informed of this circumstance before the interchangeable head is completely detached from the shaft of the endoscope. However, a comparable effect is also achieved when the positioning pins serve the purpose not of signal transmission, but the latter is performed via contacts at the coupling point, as was described previously.

In conjunction with the inventive refinement that the user is warned of a loosening of the interchangeable head by a degradation of the transmitted image, the previously mentioned positioning pins have the further advantage that the positioning pins can still maintain the connection between the interchangeable head and the shaft while the user is already being warned of the loosening of the interchangeable head. In other words, the user is already warned of a loosening of the interchangeable head, and of the risk of its falling off, while the interchangeable head is still held connected to the shaft of the endoscope via the positioning pins.

In a further preferred refinement, there is arranged between the interchangeable head and the distal end of the shaft at least one elastic element that upon loosening of the interchangeable head distances the latter from the distal end of the shaft.

Such an elastic element between the shaft and interchangeable head, for example a spring or an elastomer, has the effect that an enlarged spacing and thus the image impairment to be produced always result as the interchangeable head loosens.

It is thereby possible advantageously to prevent possible loosening of the union nut between the interchangeable head and the distal end of the shaft, and to prevent the possibility that this cannot, however, be noticed through the possibly still close-fitting contact between the interchangeable head and the distal end of the shaft.

It is further preferred in this case when the distancing is limited to less than the length of the at least one positioning pin.

Owing to this measure, it is advantageously possible in conjunction with the antiloss safeguard to prevent the elastic element from knocking the interchangeable head completely off the distal end of the shaft in the event of loosening of the interchangeable objective, and the subsequent loss of the interchangeable head. The limitation can be implemented, for example, by a stop or by virtue of the fact that in the unstressed state the elastic element has a longitudinal extension that is smaller with reference to the distal end of the shaft than the length of the at least one positioning pin, such that the interchangeable head is still held on the shaft by the positioning pin.

In a further preferred refinement, at least one operating element is arranged in the interchangeable head.

With this refinement, in addition to the function of transmission of images and light, the interchangeable head can be assigned additional functions, for example the at least one operating element can acquire auxiliary functions for imaging, such as focusing, zoom, changing the direction of view, image rotation, active and passive sensor functions, for example for spacing, pressure, temperature, vibrations, surface hardness, ultrasound reflection, layer thickness, dielectric constant, magnetic permeability, refractive index, induced eddy currents, electromagnetic fields, radar, lidar, ionizing radiation, thermal capacity, electric and thermal conductivities, pH values, chemical substance concentrations, moisture content, fluorescence, deep optical backscattering, etc., as well as processing functions such as gripping, removing, grinding, drilling, sawing, water jet processing, sandblasting, blasting with gases, heating, cooling, laser processing, etc. "Operating element" is to be understood entirely generally in this sense.

It is preferred in this case when the at least one operating element can be connected to the distal end of the shaft by means of a plug.

This refinement is advantageous, in particular for operating elements that are dependent on an electric power supply, since then the power supply for the at least one operating element can also be disconnected and easily restored at the coupling point via the plug.

Further advantages emerge from the following description and the attached drawing.

It goes without saying that the abovementioned features, and those still to be explained below, can be used not only in the respectively specified combination, but also in other combinations or on their own, without departing from the scope of the present invention.

BRIEF DESCRIPTION OF THE DRAWINGS

Preferred exemplary embodiments of the invention are illustrated in the drawing and explained in more detail in the following description. In the drawing:

FIGS. 2a) and b) show the endoscope in FIG. 1 in the region of the coupling point between the interchangeable head and the distal end of the shaft of the endoscope, in separate illustrations, FIG. 2a) showing the interchangeable head and FIG. 2b) the distal end of the shaft;

FIG. 3 shows a longitudinal section, partially cut away, through the interchangeable head, in a position rotated by comparison with FIG. 2a);

FIG. 4 shows a longitudinal section through the distal end of the shaft in FIG. 2b);

FIG. 5 shows a front view of the distal end of the shaft of the endoscope;

FIGS. 6a) and b) show the interchangeable head and the distal end of the shaft in longitudinal section, FIG. 6a) showing a state in which the interchangeable head is loosened from the distal end of the shaft of the endoscope, and FIG. 6b) showing a state in which the interchangeable head is firmly connected to the distal end of the shaft;

DETAILED DESCRIPTION OF PREFERRED EMBODIMENTS

Figure 1:
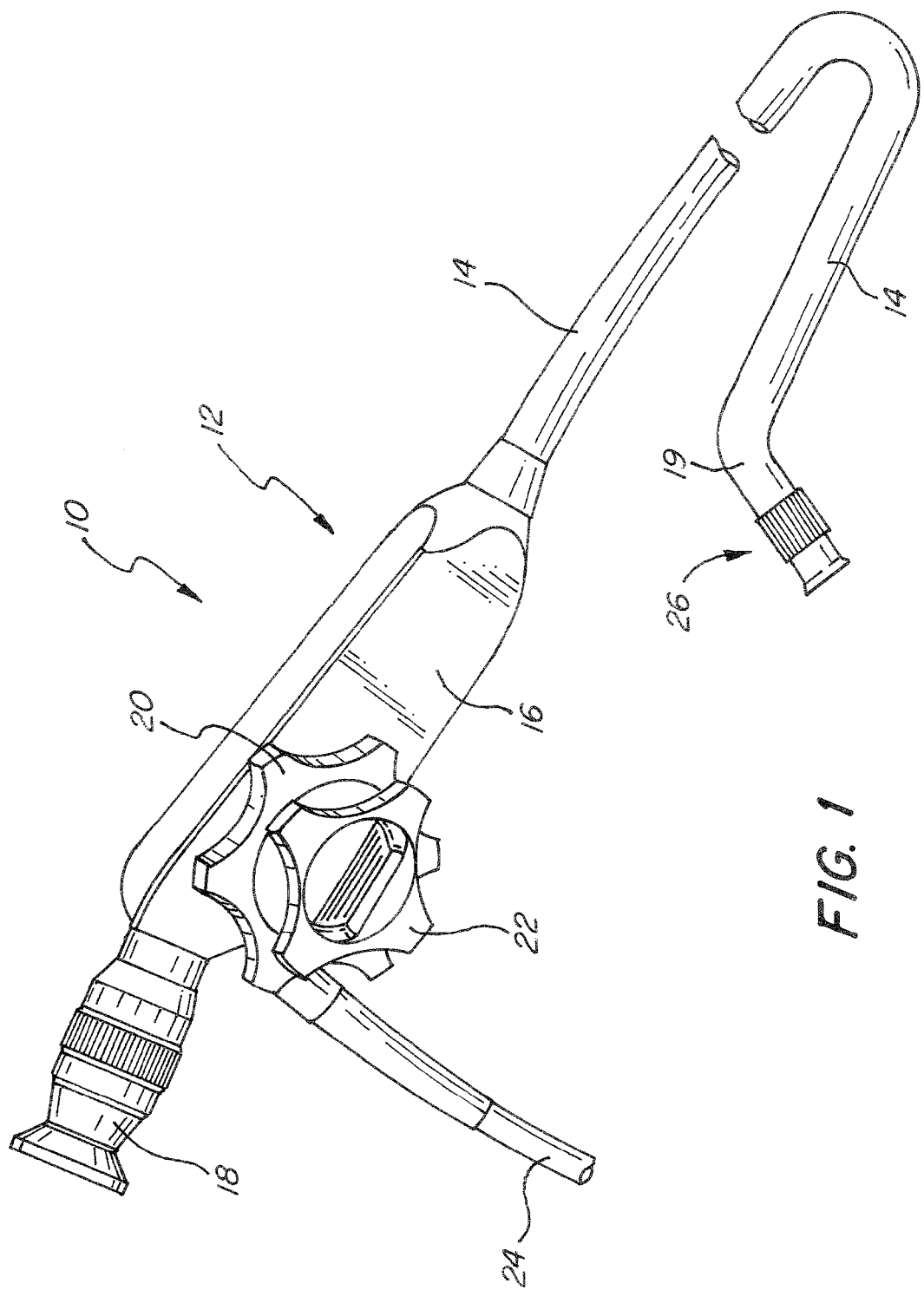
FIG. 1 shows an endoscope having an interchangeable head in a perspective overall illustration in accordance with a first exemplary embodiment.

FIG. 1 illustrates an optical instrument provided with the general reference numeral 10. In the exemplary embodiment shown, the optical instrument 10 is an endoscope 12, but the invention is not limited to such an instrument.

The endoscope 12 has an elongated shaft 14. In the exemplary embodiment shown here, the shaft 14 is flexible in such a way that, apart from a straight course, the shaft 14 can also adopt a curved course, as is illustrated in FIG. 1 by way of example.

The endoscope 12 is used as a technical endoscope in the inspection of machines, for example aircraft engines. The endoscope 12 can also be used for operating purposes in the field of minimally invasive surgery.

The endoscope 12 has an operating part 16 at the proximal end of the shaft 14. Arranged at the proximal end of the operating part 16 is an eyepiece 18 that constitutes part of a transmission system, described in yet more detail later, of the endoscope 12 for the purpose of transmitting image information. Direct observation with the eye is possible through the eyepiece 18, or a camera (not illustrated) can be connected to the eyepiece 18, the camera then being connected to an image reproduction unit, for example a monitor, on which the area observed with the endoscope 12 is visually represented.

As in the case of flexible endoscopes, the endoscope 12 is usually fitted with a deflecting mechanism for deflecting a distal end 19 of the shaft 14. The deflecting mechanism comprises a mechanism (not illustrated in more detail) that can be actuated via a first positioning wheel 20 and a second positioning wheel 22 on the operating part 16.

The deflecting mechanism works in two independent deflecting directions, the first positioning wheel 20 and the second positioning wheel 22 each being assigned to one deflecting direction.

Furthermore, there is connected to the endoscope housing 16 a fiber-optics cable 24 that is connected to an external light source (not illustrated) for feeding illuminating light into the endoscope 12.

An interchangeable head 26 is detachably connected at a coupling point 30 to the distal end 19 of the shaft 14.

Details of the interchangeable head 26 and the coupling point 30 are illustrated in FIGS. 2 to 6.

The endoscope 12 further has a transmission system 32 for transmitting illuminating power, which is formed here from two fiber bundles 34 that extend in parallel from the distal end 19 of the shaft 14 through the shaft 14 and the fiber-optics cable 24 as far as the connector (not illustrated) for connecting the fiber-optics cable 24 to a light source (not illustrated). The transmission system 32 for transmitting illuminating power is therefore completely based in the present exemplary embodiment on the transmission of light waves.

The transmission system 32 likewise has two fiber bundles 36 that extend continuously through the interchangeable head 26 and, in the state of the interchangeable head 26 connected to the distal end 19 of the shaft 14, cooperate with the fiber bundles 34, that is to say pass through the coupling point 30.

The endoscope 12 further has a transmission system 38 for transmitting image information that consists, here, of an ordered fiber bundle 40 that extends through the shaft 14 from the distal end 19 up to the proximal end of the endoscope housing 16, that is to say up to the eyepiece 18. In the present exemplary embodiment, the transmission system 38 is likewise based completely on the transmission of light waves.

The transmission system 38 further has an imaging optics 42 that is arranged in the interchangeable head 26 and, in the coupled state of the interchangeable head 26, launches the image information into the ordered fiber bundle 40 of the shaft 14.

The imaging optics 42 of the interchangeable head 26 consists of a series connection of various lenses that are illustrated in FIGS. 6a) and 6b) by appropriately curved surfaces.

The ordered fiber bundle 40 of the shaft 14 is protected at its distal end with the aid of a plane-parallel cover glass 44. The cover glass 44 does not have an optically imaging effect. The entire imaging optics 42 of the endoscope 12 is arranged in the interchangeable head 26 such that no image information is transmitted through the endoscope 12 with the interchangeable head 26 completely removed, as in FIGS. 2a) and b) and FIGS. 3 and 4.

However, in an alternative design that is not illustrated here, the imaging optics 42 can also be arranged partially in the interchangeable head 26 and partially in the shaft 14, the part of the imaging optics 42 arranged in the shaft 14 then preferably being exchangeable.

Furthermore, the ordered fiber bundle 40 is coated with a protective sheath 46.

Because of the complete arrangement of the imaging optics 42 in the interchangeable head 26, whereas the shaft 14 does not have an optical imaging system of such type, the quality of the image information transmitted by the transmission system 38 is degraded as soon as the interchangeable head 26 is slightly loosened from the distal end 19 of the shaft 14. This state is illustrated in FIG. 6a). In the case of an excessive slit formation, such as occurs in FIG. 6a), as a consequence of loosening of the interchangeable head 26, the image sharpness that can be observed through the eyepiece 18 is greatly reduced, as a result of which the user of the endoscope 12 is made aware of a loosening of the interchangeable head 26.

At the coupling point 30, the interchangeable head 26 and the distal end 19 of the shaft 14 further have flat and preferably polished surfaces 48 (interchangeable head 26) and 50 (distal end 19 of the shaft 14).

As is illustrated in FIG. 6a), upon loosening of the interchangeable head 26 illuminating light 35 enters the ordered fiber bundle 40 of the transmission system 38 from the fiber bundles 34 by reflections at the surface 48 of the interchangeable head 26, such that the user perceives a clearly brighter image given such a loosening of the interchangeable head 26.

By contrast, given an interchangeable head 26 that is completely connected to the distal end 19 of the shaft 14 in a proper way, as is illustrated in FIG. 6b), no illuminating light leaks from the transmission system 32 into the transmission system 38. A reduction in contrast of the image observed through the eyepiece 18 occurs, however, given an enlargement of the slit between the interchangeable head 36 and the distal end 19 as soon as the slit is enlarged beyond a critical minimum, and so the user is also warned by the turbidity or brightening of the image about a loosening of the interchangeable head 26.

As already mentioned, the surfaces 48 and 50 are preferably polished flat.

Furthermore, the interchangeable head 26 is connected at the coupling point 30 to the distal end 19 of the shaft 14 via two positioning pins 52 and 54 that are fastened on the interchangeable head 26, corresponding bores 56 and 58 being recessed in the distal end 19 of the shaft 14.

In cooperation with the bores 56 and 58, the positioning pins 52 and 54 serve, on the one hand, to position the interchangeable head 26 exactly relative to the distal end 19 of the shaft 14 so that the imaging optics 42 of the interchangeable head 26 cooperates exactly with the ordered fiber bundle 40. This ensures an exact image alignment and image sharpness.

On the other hand, in cooperation with the bores 56 and 58, the positioning pins 52 and 54 have the effect of securing the interchangeable head 26 on the shaft 14 in terms of rotation.

Even when loosening has already occurred, as illustrated in FIG. 6a), the positioning pins 52 and 54 still maintain a connection to the distal end 19 of the shaft 14. As previously described, when the user is already warned about the loosening of the interchangeable head 26 by a degradation of the image quality, that is to say an occurrence of blurring and/or by turbidity or brightening of the image, although it is loose the interchangeable head 26 is still connected to the shaft 14, and so the endoscope can still be withdrawn, together with the interchangeable head 26, in good time from the observation area before the interchangeable head 26 becomes completely detached.

Finally, the interchangeable head 26 can be screwed (compare FIG. 6b) to the distal end 19 of the shaft 14 by means of a union nut 60 that is captively secured on the interchangeable head 26 and can be displaced on the interchangeable head 26 in the non-coupled state of the interchangeable head 26 (compare FIG. 2a) in which the union unit 60 can be displaced completely in the distal direction). In the screwed state of the interchangeable head 26, moreover, the effect of the surfaces 48 and 50 lying flat on one another is to avoid ingress of dust and liquids and other contaminants into the coupling point 30 between the interchangeable head 26 and the shaft 14.

Furthermore, there is arranged between the interchangeable head 26 and the distal end 19 of the shaft 14 an elastic element 68 that, upon loosening of the interchangeable head 26, distances the latter from the distal end 19 of the shaft 14. In the exemplary embodiment shown, the elastic element 68 is designed in the form of a small compression spring that is embedded, for example, in the distal end 19 of the shaft 14. Upon loosening of the interchangeable head 26, the elastic element 68 presses the interchangeable head 26 away from the distal end 19 of the shaft 14 as early as when the union nut 60 is loosened, the result of this being, in the event of loosening of the union nut 60, to prevent the interchangeable head 26 from remaining in close contact with the distal end 19 of the shaft 14, and to prevent the user from thereby not being able to establish any change in the image information. However, in order to prevent the elastic element 68 from undesirably completely repelling the interchangeable head 26 when the union nut 60 is completely detached, the spacing of the interchangeable head 26 by the elastic element 68 is limited to a length that is less than the length of the positioning pin 52 or 54, such that even with the elastic element 68 completely unstressed a connection still exists between the interchangeable head 26 and the shaft 14 via the positioning pins 52 and 54, with the result that it is possible at least to prevent the interchangeable head 26 from falling off.

Figure 7:
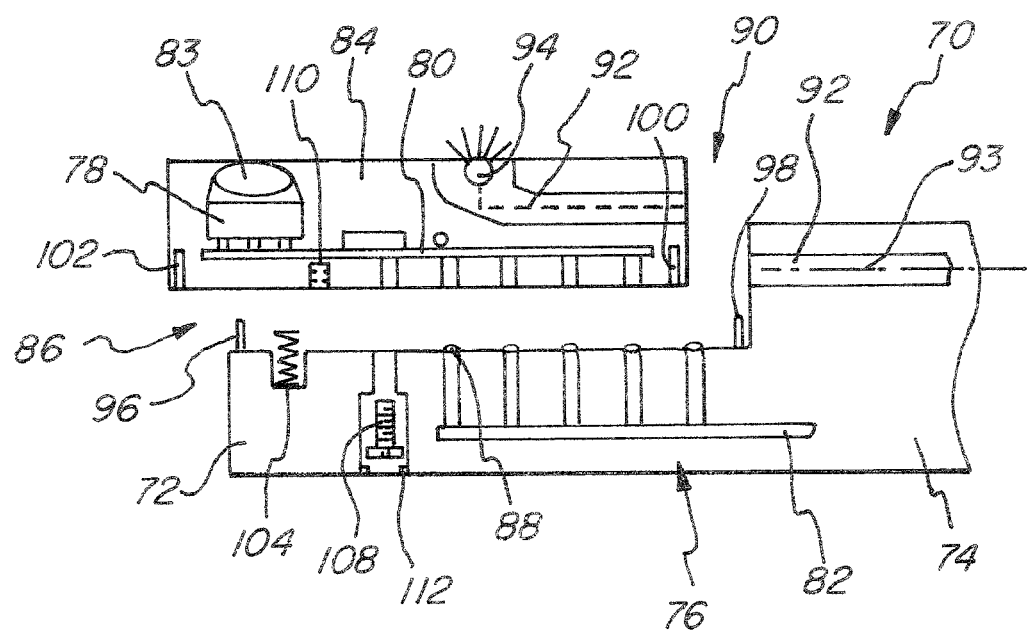
FIG. 7 shows a distal end of an optical instrument in accordance with a further exemplary embodiment having an interchangeable head, in a schematic side view in a state in which the interchangeable head is detached from the distal end of the shaft.

In refinements that are not illustrated, the previously mentioned positioning pins 52 and 54 can also be used to transmit electric signal s or power, for example whenever the interchangeable head has an optoelectronic image pick-up (video image sensor) (compare also the subsequent exemplary embodiment in accordance with FIG. 7), it then being possible for the electric signal s to be transmitted correspondingly through the coupling point via at least one of the pins. In such a refinement, the electrically conducting connection between at least one of the positioning pins 52 or 54 and the corresponding bore 56 or 58 can be designed such that the transmission of signals is interrupted as early as during a loosening of the interchangeable head from the distal end of the shaft, as a result of which the image disappears and the user is thereby warned about the loosening.

Also illustrated in FIGS. 2a) and b) are two marks 62 and 64 that permit a coarse preliminary orientation of the interchangeable head 26 upon mounting of the latter on the shaft 14, in order to facilitate the insertion of the positioning pins 52 and 54 into the bores 56 and 58.

Furthermore, the positioning pins 52 and 54 can be removed from the interchangeable head 26, and so they can easily be exchanged in the case of bending or some other form of damage.

Instead of the fiber bundle 40 in the shaft 14, it is also possible to arrange behind the cover glass 44 in the region of the distal end 19 of the shaft 14 an electronic image pick-up (not illustrated) that is connected to a video monitor unit via a signal line leading in the proximal direction. In the case of such a variant, the imaging optics 42 is again arranged completely in the interchangeable head 26 or partially in the interchangeable head 26 and partially in the shaft 14. Upon loosening of the interchangeable head 26, the image pick-up is then no longer situated exactly in the image plane of the imaging optics 42, as a result of which perceptibly modified image information is transmitted in the proximal direction.

Illustrated in FIG. 7 as a further exemplary embodiment is an optical instrument, denoted by the general reference numeral 70, in the region of a distal end 72 of its shaft 74.

The optical instrument 70 is an endoscope, for example, the shaft 74 being rigid, for example.

This optical instrument 70 has a transmission system 76 for transmitting image information from distal to proximal ends, which has an optoeletronic image pick-up (video image sensor) 78 whose image information is conducted in the proximal direction in the form of electric signal s via electric signal lines 80 and 82.

The optoelectronic image pick-up 78, upstream of which an imaging optics 83 is connected, is not arranged in the shaft 74 of the instrument 70, however, but in an interchangeable head 84 that can be removed from the shaft 74. In the state of the interchangeable head 84 connected to the shaft 74, the electric signal lines 80 and 82 pass through a coupling point 86, the coupling point 86 being appropriately fitted with a plurality of contacts 88 on the interchangeable head side and shaft side.

The image pick-up 78 and the imaging optics 83 can also be designed as a complete camera unit.

Upon loosening of the interchangeable head 84, the contacts 88 are correspondingly opened and the conduction of signals by the electric signal lines 80 and 82 is correspondingly interrupted as a result, and so no further image information can be transmitted in the proximal direction from the image pick-up 78, and thus the image disappears for the observer.

The instrument 70 further has a transmission system 90 for transmitting illuminating power from proximal end to distal end, which is formed, in turn, by an optical waveguide 92 in the form of a fiber bundle that passes through the coupling point 86 in the state of the interchangeable head 84 connected to the shaft 74.

Instead of an optically conducting transmission system for transmitting illuminating power, such a system can, however, also be based on an electric power line 93 that is interrupted in the region of the coupling point 86 in the case of a loosening of the interchangeable head 84, there then being arranged in the interchangeable head 84 a light source 94, for example in the form of an LED, which is correspondingly extinguished upon loosening of the interchangeable head 84, the result being the occurrence of a perceptible darkening of the transmitted image.

Furthermore, provided, in turn, in the exemplary embodiment illustrated in FIG. 7 are positioning pins 96 and 98 that engage in corresponding bores 100 and 102 in the interchangeable head 84 in order to ensure exact positioning of the interchangeable head 84 with reference to the distal end 72 of the shaft 74, and thus ensure exact closure of the contacts 88 between the shaft 74 and the interchangeable head 84.

Also provided, in turn, is an elastic element 104 that, upon loosening of the fastening element 108 in the anchorage 110, distances the interchangeable head 84 such that the image information is noticeably modified by opening of at least one contact. The fastening element 108 is captively secured by a ring 112.

The orientation of the surfaces of the coupling point 86 was selected arbitrarily in this exemplary embodiment.

Figure 8:
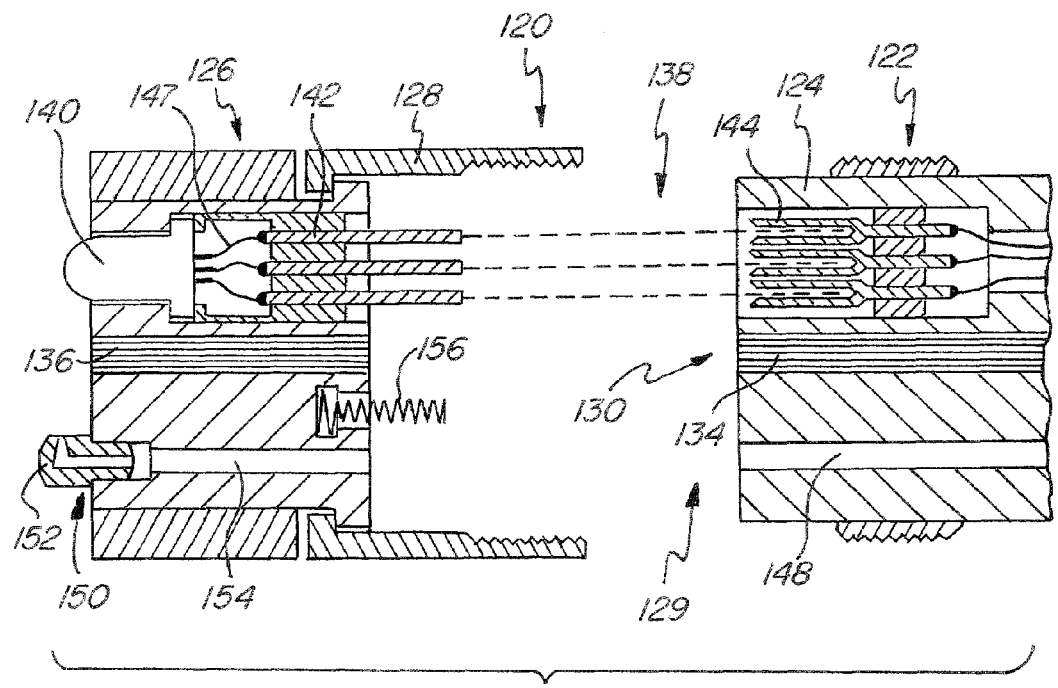
FIG. 8 shows a distal end of an optical instrument in accordance with a further exemplary embodiment, having an interchangeable head with a complete integrated camera, in longitudinal section in the state removed from the distal end of the shaft.

A further optical instrument, in particular an endoscope, provided with the general reference numeral 120 is illustrated by a detail in the region of its distal end in FIG. 8. This exemplary embodiment can be implemented, in particular, in the case of the endoscope 12 in FIG. 1.

The instrument 120 has a shaft 122, which is illustrated in FIG. 8 only in the region of its distal end 124.

The instrument 120 further has an interchangeable head 126, which can be fastened through screwing by means of a union nut 128 on the distal end 124 of the shaft 122. A coupling point between the interchangeable head 126 and the distal end 124 of the shaft 122 is denoted by 129.

The instrument 120 has a first transmission system 130 for transmitting illuminating power in the distal direction, which system has an optical waveguide 134 arranged in the shaft and an optical waveguide 136 arranged in the interchangeable head.

The instrument 120 also has a second transmission system 138, for transmitting image information in the proximal direction, which, like the first transmission system 130, likewise passes through the coupling point 129 when the interchangeable head 126 is fastened on the shaft 122. The transmission system 138 for transmitting image information has an image pick-up 140, arranged in the interchangeable head 126, in the form of a complete camera, in particular a miniaturized camera. The transmission system 138 also has an electric signal line 141 that leads in the proximal direction from the image pick-up 140 through the coupling point 129 when the interchangeable head 126 is fastened on the shaft 122.

A total of three signal lines 141 are illustrated in FIG. 8, these being designed as a plug-in contact. For this purpose, the signal lines 141 have contact fingers 142 integrated in the interchangeable head 126, and arranged at the distal end 124 of the shaft 122 are contact plugs 144, of which there are a corresponding number and in which the contact fingers 142 engage upon connecting the interchangeable head 126 to the distal end 124 of the shaft 122.

The instrument 120 further has a channel 148 through which, for example, a gas or a liquid can be conducted from the proximal to the distal ends. The interchangeable head 126 has an operating element 150 that is designed as a nozzle 152 that is arranged at the distal end of a channel 154 constructed in the interchangeable head 126. In this arrangement, the channel 154 is aligned with the channel 148 when the interchangeable head 126 is connected to the shaft 122. The nozzle 152 can serve the purpose, for example, of directing the fluid, fed through the channel 148 and further through the channel 154, onto the end of the image pick-up 140 on the light entry side, in order, for example, to keep this end free from contaminants. Furthermore, there is provided on the interchangeable head 126 an elastic element 156 that can serve, for example, as in the previous exemplary embodiment to distance the interchangeable head 126 from the distal end 124 of the shaft 122 when the union nut 128 is loosened or becomes loose.

Figure 9:
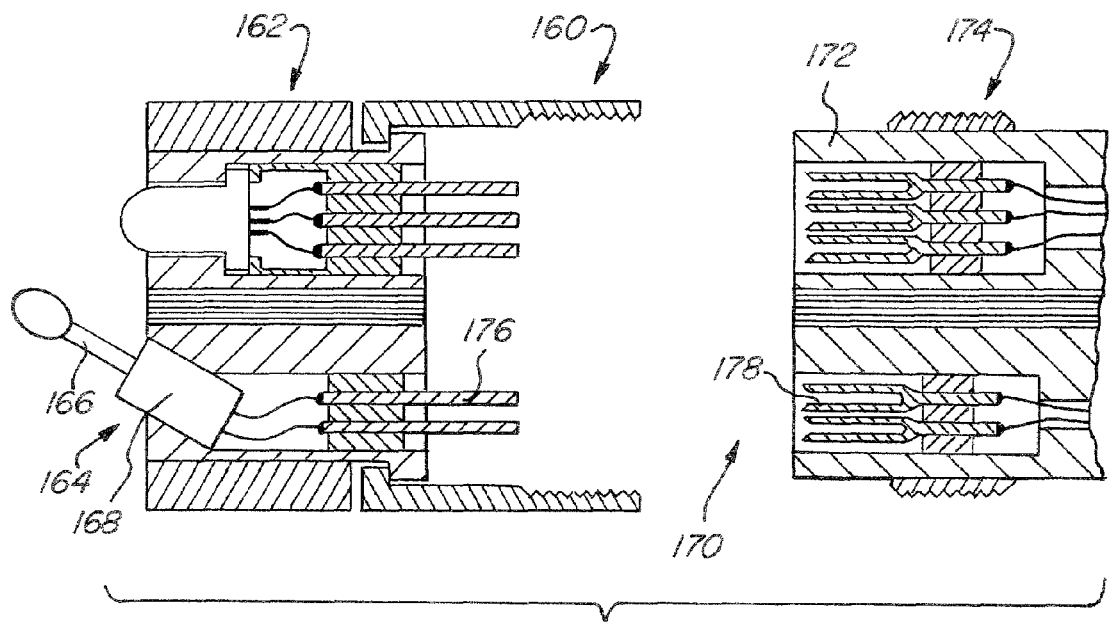
FIG. 9 shows a distal end of an optical instrument in accordance with a further exemplary embodiment, having an interchangeable head with a complete integrated camera, in longitudinal section in the state removed from the distal end of the shaft.

Illustrated in FIG. 9 is a further exemplary embodiment of an optical instrument 160, which is described below only with reference to the differences from the instrument 120.

An interchangeable head 162 of the instrument 160 has an operating element 164 that is, for example, a processing tool 166 with a motor 168. The processing tool 166 is, for example, a drill, milling cutter, grinder or the like. Provided at a coupling point 170 between the interchangeable head 162 and a distal end 172 of a shaft 174 of the instrument 160 for the purpose of supplying electric power to the operating element 164 are plug-in contacts that have contact fingers 176, arranged on the interchangeable head 162, and contact plugs 178 that are arranged at the distal end 172 of the shaft 174 and in which the contact fingers 176 engage upon fastening the interchangeable head 162 on the shaft 174.

In this exemplary embodiment, the interchangeable head 162 therefore takes over not only the function of image transmission and illumination, but also the function of a processing instrument, which is fully integrated in the interchangeable head 162.

Figure 10:
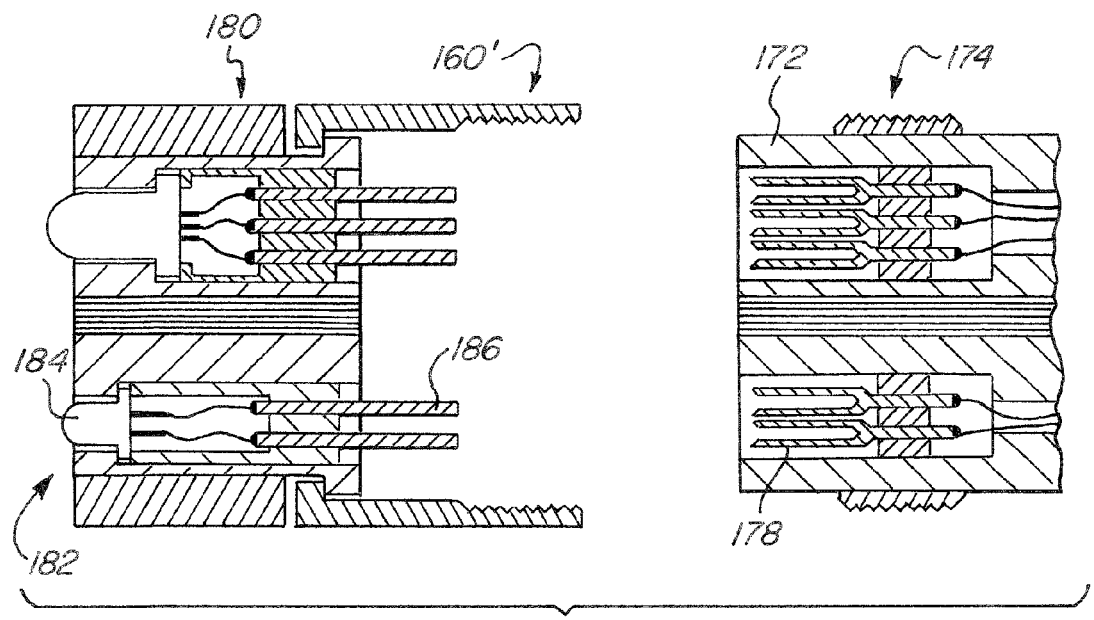
FIG. 10 shows a distal end of an optical instrument in accordance with a further exemplary embodiment having an interchangeable head with integrated camera, in longitudinal section in the state removed from the distal end of the shaft.

Illustrated in FIG. 10 is an exemplary embodiment, modified slightly by comparison with FIG. 9, of an instrument 160', which does not differ from the instrument 160 with regard to the shaft 174, but merely with regard to an interchangeable head 180 which, instead of the processing tool 166 with motor 168, has as operating element 182 a light source 184, for example a UV light-emitting diode, for carrying out inspections with fluorescent light. As emerges from FIG. 10, for the purpose of supplying electric power, the operating element 182 has contact fingers 186 that are advantageously compatible with the contact plugs 178 of the shaft 174 such that the interchangeable head 180 can be fastened on the same shaft 174 as the interchangeable head 162.

Figure 11:
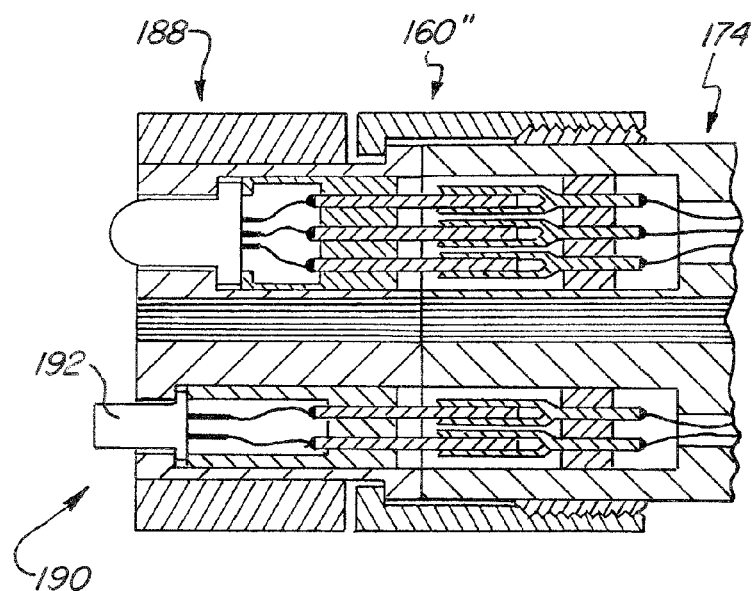
FIG. 11 shows a distal end of an optical instrument in accordance with a further exemplary embodiment having an interchangeable head with integrated camera, in longitudinal section in the state connected to the distal end of the shaft.

A further interchangeable head 188, compatible with the shaft 174, is illustrated in FIG. 11, and together these correspondingly form an instrument 160".

As operating element 190, the interchangeable head 188 has a sensor 192 that is, for example, capable of detecting physical or chemical states. It is also illustrated in FIG. 11 how the plug-in contacts are joined in the state when the interchangeable head 188 is fastened on the shaft 174.

Figure 12:
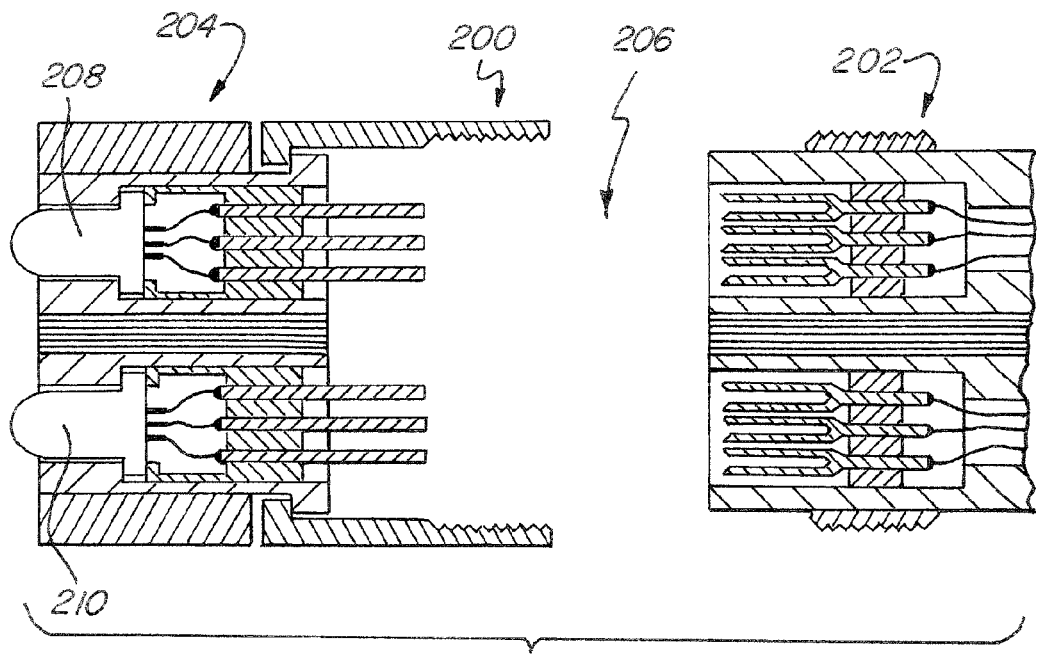
FIG. 12 shows a distal end of an optical instrument in accordance with a further exemplary embodiment having an interchangeable head with two integrated cameras, in longitudinal section in the state removed from the distal end of the shaft.

Illustrated in FIG. 12 is a further instrument, which is provided with the general reference numeral 200 and has a shaft 202 and an interchangeable head 204 that differs from the preceding exemplary embodiments in that a transmission system 206 for transmitting image information in the proximal direction has two image pick-ups 208 and 210, which are both arranged in the interchangeable head 204. Both image pick-ups 208 and 210 are, in turn, preferably designed as complete miniaturized cameras.

Figure 13:
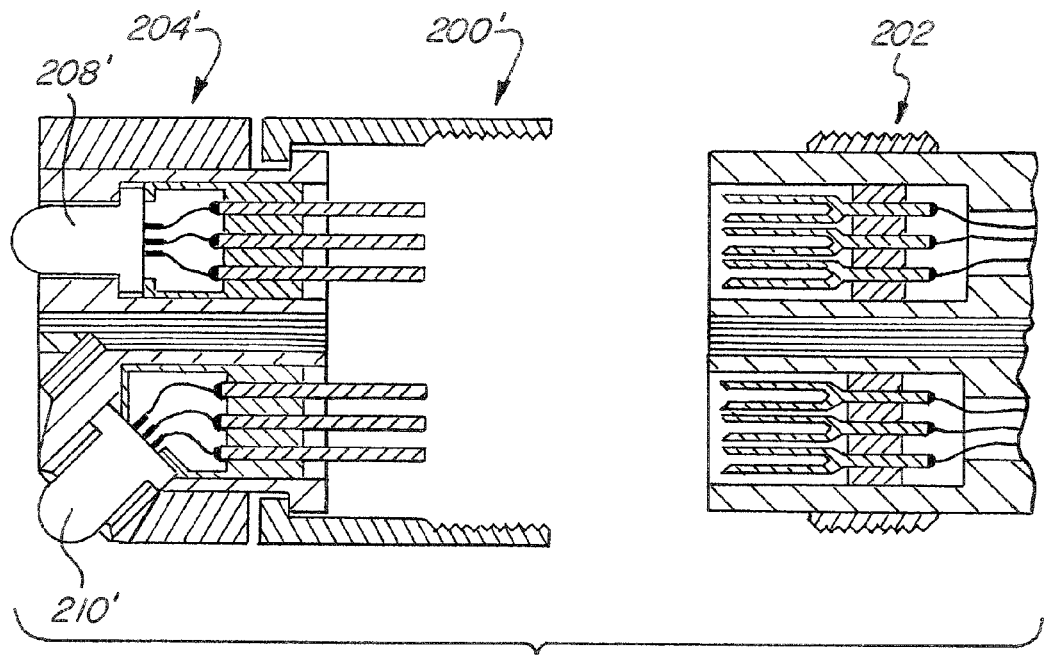
FIG. 13 shows a distal end of an optical instrument in accordance with a further exemplary embodiment having an interchangeable head with two integrated cameras, in longitudinal section in the state removed from the distal end of the shaft.

Whereas, in the case of the exemplary embodiment illustrated in FIG. 12, both image pick-ups 208 and 210 are arranged in the interchangeable head 204 in parallel alignment relative to one another in a configuration for looking straight ahead, in FIG. 13 the image pick-up 210' is not aligned parallel to the other image pick-up 208', but looking at it in an inclined fashion, in an exemplary embodiment 200' modified slightly by comparison with the instrument 200.

The signal lines for the image pick-ups 208, 210 or 208' and 210' are correspondingly designed as plug-in contacts that permit the interchangeable heads 204 and 204' to be handled easily when being exchanged.

In the case of the exemplary embodiments illustrated in FIGS. 12 and 13, as well, there is the advantageous possibility of providing only one and the same shaft 202, while the interchangeable heads 204 and 204' can be fastened on the shaft 202 such that they can be exchanged for one another, because the plug-in contacts for connecting the corresponding signal line are of universal configuration.

In the case of the exemplary embodiments illustrated in FIGS. 8 to 13, it is possible, if appropriate, to notice a loosening of the respective interchangeable head by a degradation of the image quality, as with the previous exemplary embodiment.

What is claimed is:

1. An optical instrument, comprising:
   a shaft having a distal end;
   an interchangeable head detachably connected to said distal end of said shaft at a coupling point;
   a first transmission system for transmission of illuminating power in a distal direction, said first transmission system being arranged partially in said shaft and partially in said interchangeable head and passing through said coupling point;
   a second transmission system for transmission of image information in a proximal direction, said second transmission system being arranged partially in said shaft and partially in said interchangeable head and passing through said coupling point;
   at least one of said interchangeable head and said coupling point being designed in such a way that upon loosening of said interchangeable head image information of perceptively modified quality is transmitted by said second transmission system;
   wherein said interchangeable head is connected to said distal end of said shaft at said coupling point by means of at least two positioning pins that engage in corresponding bores;
   wherein there is arranged between said interchangeable head and said distal end of said shaft an elastic element that upon loosening of said interchangeable head distances said interchangeable head from said distal end of said shafts; and
   wherein said distancing is limited to less than a length of said positioning pins.

2. The instrument of claim 1, wherein said first transmission system comprises an optical waveguide that extends through said shaft and through said interchangeable head, and is interrupted at said coupling point, and wherein said distal end of said shaft and said interchangeable head each have a flat polished surface at said coupling point.

3. The instrument of claim 1, wherein said at least two positioning pins are provided on said interchangeable head, and said bores are provided on said distal end of said shaft.

4. The instrument of claim 1, wherein at least one of the positioning pins serves the purpose of transmitting electric signals or electric power.

5. The instrument of claim 1, wherein at least one operating element is arranged in said interchangeable head.

6. The instrument of claim 5, wherein said at least one operating element can be connected to said distal end of said shaft by means of a plug.

7. The instrument of claim 1, wherein said second transmission system has imaging optics, said imaging optics being arranged partially in said interchangeable head and partially in said shaft, a part of said imaging optics arranged in said shaft is exchangeable in said shaft, wherein said part of said imaging optics arranged in said shaft comprise a first imaging part that is exchangeable with a second imaging part; wherein said first imaging part corresponds to a first interchangeable head and said second imaging part corresponds to a second interchangeable head.

8. The instrument of claim 1, wherein said second transmission system has imaging optics, said imaging optics being arranged partially in said interchangeable head and partially in said shaft, a part of said imaging optics arranged in said shaft is exchangeable in said shaft, wherein said part of said imaging optics arranged in said shaft comprise a first imaging part that is exchangeable with a second imaging part and said first imaging part differs from said second imaging part with respect to an optical property.

9. An optical instrument, comprising:
a shaft having a distal end;
an interchangeable head detachably connected to said distal end of said shaft at a coupling point;
a first transmission system for transmission of illuminating power in a distal direction, said first transmission system being arranged partially in said shaft and partially in said interchangeable head and passing through said coupling point;
a second transmission system for transmission of image information in a proximal direction, said second transmission system being arranged partially in said shaft and partially in said interchangeable head and passing through said coupling point;
at least one of said interchangeable head and said coupling point being designed in such a way that upon loosening of said interchangeable head image information of perceptively modified quality is transmitted by said second transmission system;
wherein said second transmission system has imaging optics, said imaging optics being arranged partially in said interchangeable head and partially in said shaft, a part of said imaging optics arranged in said shaft is exchangeable in said shaft;
wherein there is arranged between said interchangeable head and said distal end of said shaft an elastic element that upon loosening of said interchangeable head distances said interchangeable head from said distal end of said shaft; and
wherein said interchangeable head is connected to said distal end of said shaft at said coupling point by means of at least one positioning pin that engages in a corresponding bore, and wherein said distancing is limited to less than a length of said at least one positioning pin.

* * * * *